United States Patent [19]

Kershner

[11] Patent Number: 4,515,023
[45] Date of Patent: May 7, 1985

[54] RECREATIONAL POOL IMPLEMENT
[76] Inventor: Daniel E. Kershner, 1609 Woodside Ave., Baltimore, Md. 21227
[21] Appl. No.: 478,351
[22] Filed: Mar. 24, 1983
[51] Int. Cl.³ .............................................. G01N 1/12
[52] U.S. Cl. ................................................. 73/864.51
[58] Field of Search ................ 73/864.51; 33/126.4 R; 294/19.1, 23, 97

[56] References Cited
U.S. PATENT DOCUMENTS
874,711 12/1907 Thueson ........................ 294/19.1 X
946,695 1/1910 Dinsmoor .................. 33/126.4 R X
3,960,021 6/1976 Jones ................................ 73/864.51

Primary Examiner—S. Clement Swisher
Assistant Examiner—Ellwood G. Harding, Jr.
Attorney, Agent, or Firm—Leonard Bloom

[57] ABSTRACT

A swimming pool implement comprises an elongated stick having means on the end for lifting the removable lid of a swimming pool skimmer. A rectangular water-sampling vial may be inserted into a transverse recess formed in an intermediate portion of the stick. The stick may be inserted to a desired depth into the pool, and then the stick may be withdrawn to obtain a water sample in the vial. A dual function is thereby performed by the implement.

3 Claims, 14 Drawing Figures

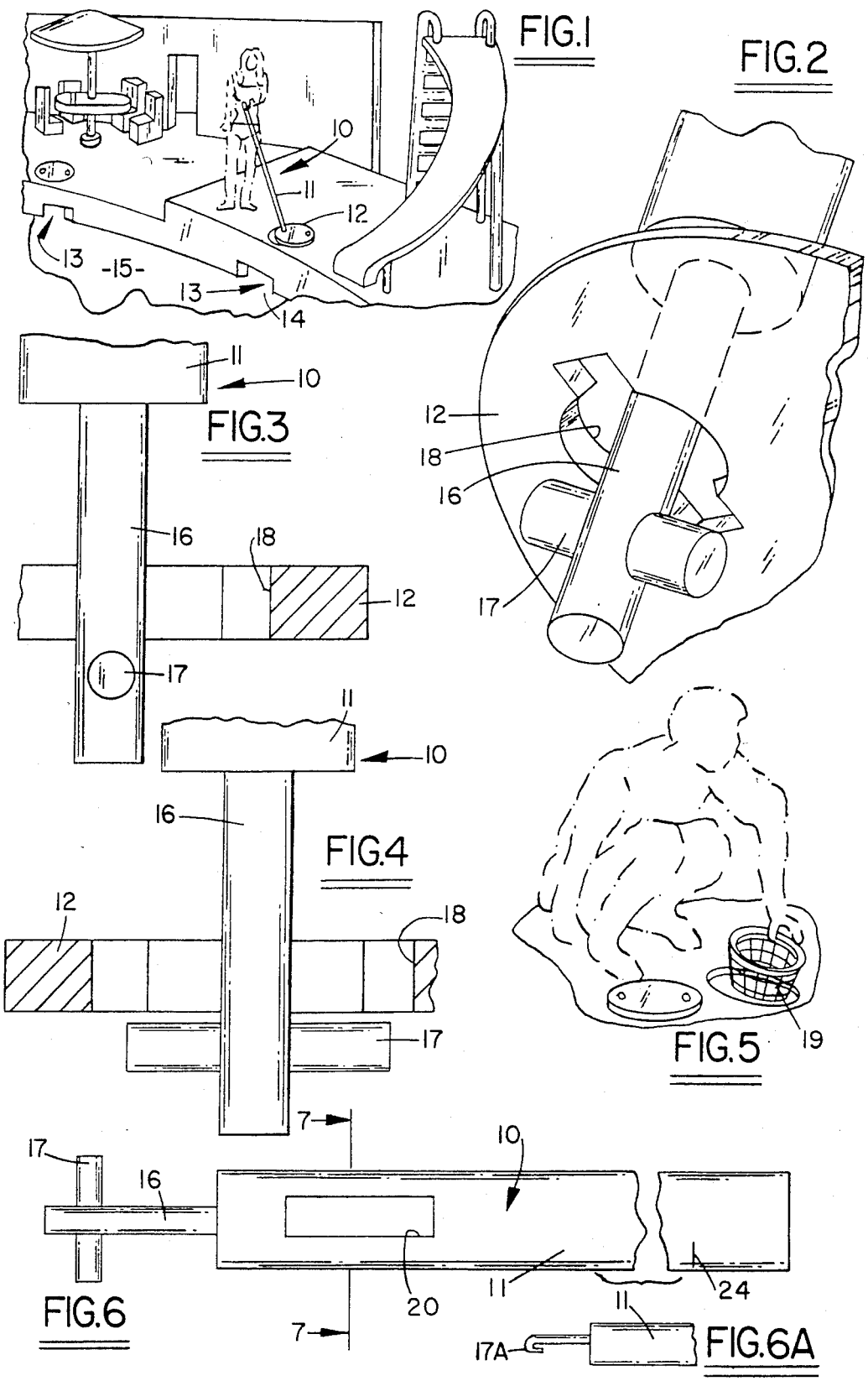

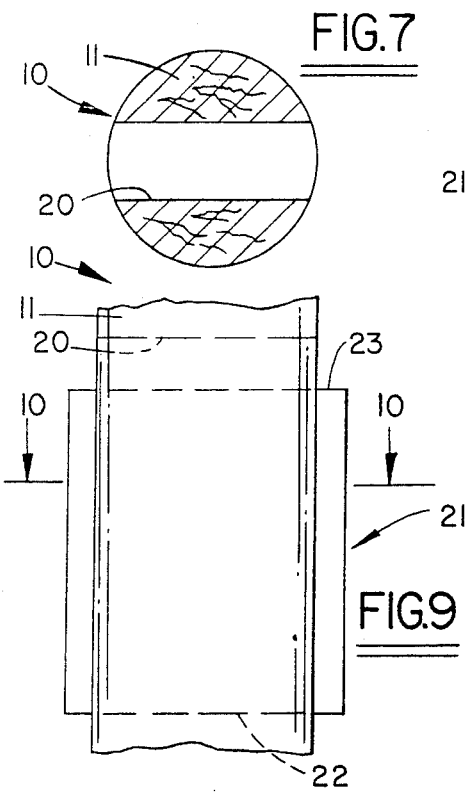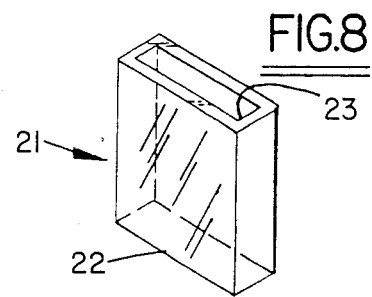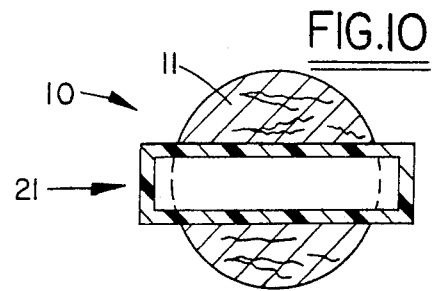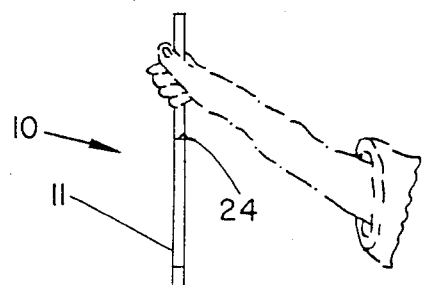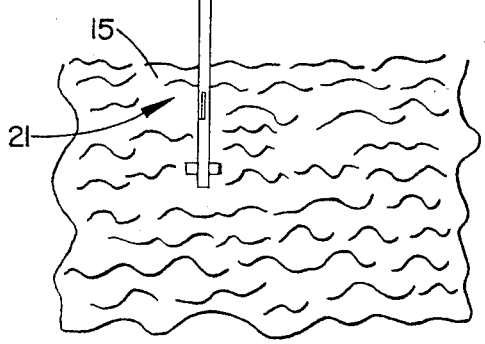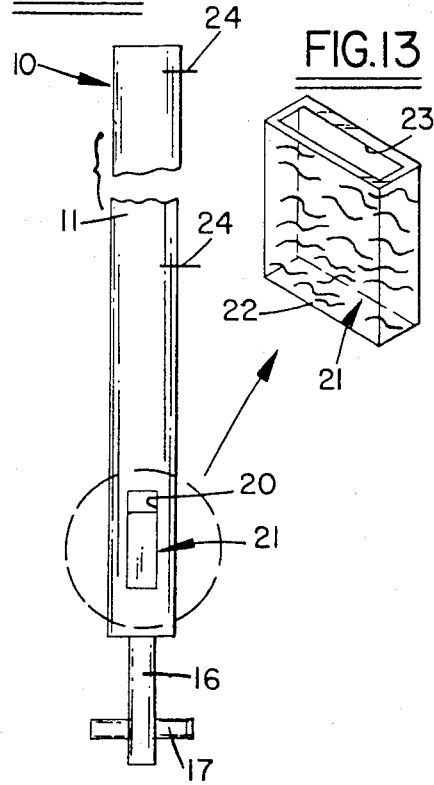

RECREATIONAL POOL IMPLEMENT

FIELD OF THE INVENTION

The present invention relates to an implement for use in recreational pool waters, and more particularly, to a combined lifter for the removable lid of a swimming pool skimmer and a water sampling device for the pool.

BACKGROUND OF THE INVENTION

Swimming pools may be provided with a plurality of "skimmers" positioned around the periphery of the pool. These skimmers are electric motor-driven pumps that continually draw off the surface water of the pool, filter it, and return the water to the pool at a point below the surface thereof. As a result, bugs, leaves, cigarette butts or other debris are effectively skimmed off the surface of the pool and are removed before sinking to the bottom of the pool. These skimmers have a removable cover or lid which is generally in the form of a circular metal or plastic plate that is substantially flush with the surface of the concrete apron adjacent to the pool. This circular plate is usually provided with an access opening, which may consist of a central hole or else a pair of diametrically-opposed recesses or notches formed in the plate. To remove the plate, the inspector's finger or a suitable implement may be inserted into one of the notches to lift the lid. The filter basket within the skimmer may then be inspected, and the contents thereof discarded prior to replacing the lid. Also, the filter basket is usually made of plastic and occasionally requires replacement.

This procedure requires the inspector (or home owner) to assume a kneeling or crouching position to lift each lid; and to preclude tampering by children, the lid may have a relatively tight fit. Thus lifting the lids on a plurality of skimmers around the pool may become uncomfortable and tiring. This is especially aggravating for municipal or governmental inspectors, as well as service personnel, who are required to examine many skimmers during the course of a day's work. Moreover, where swimming pools are located adjacent to wooded areas, small mice, frogs, snakes or lizards may occasionally find their way into the skimmer, and thus indiscriminately poking one's fingers through an access opening in the lid may become hazardous.

Additionally, for in-ground or above-ground swimming pools, hot tubs, health center spas and other recreational pools, it is necessary (or at least desirable) to maintain certain water chemistry parameters. Thus, the water in the pool must be sampled at certain intervals to run various tests, such as the chlorine level, PH level, total alkalinity, calcium hardness, total dissolved solids, algae and the like. To take individual water samples for each test, various kits are commercially available. One such testing kit, marketed by Taylor Chemical Company, includes a plurality of rectangular cross-sectioned standardized sampling tubes or vials. Each vial is molded from a clear plastic, and the vial is open at one end and closed at its other end. The inspector merely rolls up his sleeve, grips the vial, plunges it into the swimming pool to a desired depth, and lifts the vial out of the pool to obtain a sample of the water. While apparently effective for the purposes intended, this procedure is nevertheless time consuming, awkward, and somewhat messy. Moreover, it may be difficult to gauge the depth to which the vial has been plunged into the pool.

SUMMARY OF THE INVENTION

Accordingly, it is an object of the present invention to alleviate these disadvantages and deficiencies of the prior art by providing a combined skimmer lid lifter and water sampling device for swimming pools and the like.

It is another object of the present invention to provide such a combined device that may be manufactured easily and economically, and which may be sold as a swimming pool accessory for use by municipal inspectors or home owners.

It is yet another object of the present invention to provide such a combined device which may be used as a promotional item by the manufacturers of skimmers, testing kits or other accessories for swimming pools.

It is a further object of the present invention to encourage and facilitate the taking of water samples in swimming pools and other recreational waters.

In accordance with the broad teachings of the present invention, there is disclosed a lid lifter for a swimming pool skimmer and a combined water sampling device which comprises an elongated stick. First means are provided on one end of the stick for lifting the removable lid of a swimming pool skimmer, and second means are provided on an intermediate portion of the stick for sampling the water in the swimming pool.

In accordance with the further teachings of the present invention, the first means comprises a reduced cross-sectional area of the stick at the end thereof, and a prong carried by the reduced cross-sectional area and extending transversely therefrom at both sides of the reduced cross-sectional area. The second means comprises a sampling vial open at one end and closed at the other end thereof, and a transverse recess formed in the stick to receive the vial. The closed end of the vial is disposed towards the one end of the stick, and the open end of the vial extends laterally beyond the adjacent respective surfaces of the stick. As a result, the stick may be inserted into the pool and lifted out to obtain a water sample in the vial. Preferably, the vial has a rectangular cross-section, and the recess in the stick has a corresponding rectangular cross-section to receive the vial with a slight interference fit therebetween.

In a preferred embodiment, the stick comprises an elongated rod or dowel, made of wood, and having a length of approximately four feet. The stick is also provided with graduations to indicate the depth to which the stick is inserted into the pool.

These and other objects of the present invention will become apparent from a reading of the following specification, taken in conjunction with the enclosed drawings.

BRIEF DESCRIPTION OF THE DRAWINGS

FIG. 1 shows the combined swimming pool implement of the present invention, preferably in the form of an elongated stick, being used to lift up the removable lid of one of the swimming pool skimmers, thereby facilitating the inspection of the filter basket therein.

FIG. 2 is an enlarged portion of FIG. 1, showing the stick inserted through one of the notches on the lid to lift the lid.

FIG. 3 is a section view, showing the prong (which extends from the reduced cross-sectional end of the stick) disposed transversely of the notch in the lid.

FIG. 4 corresponds to FIG. 3, but shows the stick turned substantially ninety (90) degrees to aline the prong with the notch and facilitate removal of the stick from the lid.

FIG. 5 shows the filter basket being removed from the skimmer, as may be necessary.

FIG. 6 is a front elevation of the elongated stick of the present invention.

FIG. 6A (drawn to reduced scale) shows an alternate embodiment of a portion of the elongated stick of FIG. 6.

FIG. 7 is a section view, taken across the lines 7—7 of FIG. 6, and showing the transverse recess in an intermediate portion of the stick.

FIG. 8 is an isometric view of a typical water-sampling tube or vial that may be used with the implement of the present invention.

FIG. 9 is a side elevation of a portion of the stick, showing the vial inserted within the recess and retained therein by a slight interference fit.

FIG. 10 is a section view, taken across the lines 10—10 of FIG. 9, showing the open end of the vial projecting beyond the respective sides of the elongated stick.

FIG. 11 shows the stick (with the vial thereon) being plunged into the pool to a desired depth.

FIG. 12 shows the stick removed from the pool.

FIG. 13 shows the vial removed from the stick and having the desired water sample therein.

DESCRIPTION OF THE PREFERRED EMBODIMENT

With reference to FIG. 1, there is illustrated the swimming pool implement 10 of the present invention, which preferably comprises a lid lifter for a swimming pool skimmer and a combined water sampling device. The implement 10 is preferably in the form of an elongated stick 11 that may be used to conveniently lift up the removable cover or lid 12 of a swimming pool "skimmer" 13 having an inlet 14. A plurality of skimmers may be spaced around the perimeter of the swimming pool 15; however, for ease of illustration, only two skimmers are shown in FIG. 1. These skimmers are standard components used in swimming pools for home owners, municipal pools, health clubs and the like. One such skimmer is the U-3 automatic Surface Skimmer sold by Swimquip, Inc. However, the construction details of the skimmer form no part of the present invention, and being standard, have been omitted herein for ease of illustration. As shown in FIG. 1, the pool owner may use the implement 10 to lift up the lid of the skimmer (to inspect the filter basket therein) while standing. Any kneeling or crouching, which otherwise can become uncomfortable, is thereby avoided.

With reference to FIGS. 2-6, the elongated stick has a reduced cross-sectional area 16 at one end thereof. A prong 17 is carried by this reduced cross-sectional area 16 and extends transversely (preferably perpendicularly) therefrom from both sides thereof. The prong may be inserted into the notch 18 on the lid 12, and then the stick may be turned approximately ninety (90) degrees so that the prong is disposed transversely of the notch, thereby facilitating lifting of the lid as shown in FIG. 3. After the lid has been replaced on the skimmer, to remove the stick from the lid, the stick may again be turned approximately ninety (90) degrees, so that the prong is substantially alined with the notch and will clear the notch as the stick is withdrawn from the lid as shown in FIG. 4. As shown in FIG. 5, the filter basket 19 may be removed, if necessary, to either remove the contents thereof or to replace the filter basket.

With reference to FIG. 6A, a modification is illustrated, wherein the reduced portion 16 and transverse prong 17 are replaced by a metal hook 17A fastened on the end of the stick 11.

With reference again to FIG. 6, and with further reference to FIGS. 7-10, the elongated stick 11 preferably comprises a rod or dowel (preferably made of wood, like a broomstick) having a length of approximately four (4) feet. It will be appreciated by those skilled in the art that other forms of the stick, as well as other materials such as metal or plastic, are equally feasible. Preferably, however, the stick is made from a natural bio-degradable non-toxic material, such as pine wood, and is left uncoated so as not to affect, or be affected by, the chemicals in the water.

A transverse slotted recess 20 is formed in an intermediate portion of the stick, as shown in FIGS. 6 and 7, and is intended to receive a sampling tube or vial 21. As shown in FIG. 8, the vial 21 is preferably molded from a suitable plastic material, is relatively thin-walled and transparent, and has a substantially prismatic configuration and a rectangular cross-section. The vial is inserted into the slotted recess formed in the elongated stick, as shown in FIG. 9, and is retained therein by a slight interference fit. The closed end 22 of the vial is nearest to the forward (reduced cross-sectional) end of the stick. As shown more clearly in FIGS. 9 and 10, the dimensions of the vial are such that the vial (or at least the open end 23 thereof) projects laterally beyond the adjacent side surfaces of the stick. This assures that the water will enter into the vial when the stick (with the vial carried thereby) is inserted into the swimming pool.

With reference to FIGS. 11-13, the stick may be inserted or plunged into the swimming pool to a desired depth as indicated by the spaced graudations 24 on the stick. The stick may then be withdrawn, as shown in FIG. 12, and the vial may then be removed from the stick (by a simple sideways push) to obtain the water sample as shown by the partially filled vial shown in FIG. 13. As a result, the water samples may be taken frequently and conveniently without getting the user's arm or clothes wet.

The swimming pool implement of the present invention preferably serves a dual function, combined into a single implement, and one that can be manufactured easily and economically for widespread distribution and usage.

Obviously, many modifications may be made without departing from the basic spirit of the present invention. For example, the recess in the intermediate portion of the elongated stick may be modified to accommodate a pair of sampling tubes or vials carried simultaneously by the stick. The cross-sectional configuration of the recess could also be modified to accommodate other vials, tubes or sampling receptacles. Moreover, while a rigid stick is preferred, a fold-up stick is also feasible, especially when the stick is intended to be sold in a compact kit form with a plurality of vials, testing materials and instructions.

Accordingly, it will be appreciated by those skilled in the art that within the scope of the appended claims, the invention may be practiced other than has been specifically desired herein.

I claim:

1. A water sampling device for a swimming pool or other recreational body of water, comprising an elongated stick having an intermediate portion with a transverse recess formed therein, and a vial received in the recess with a slight interference fit, whereby the vial is secured within the recess but may be removed manually therefrom, the vial having an open end and a closed end, the closed end being disposed towards the end of the stick, and the open end of the vial extending laterally beyond both adjacent surfaces of the stick, whereby the stick may be inserted into the pool and lifted out to obtain a water sample in the vial.

2. The device of claim 1, wherein the recess in the stick has a rectangular cross-section, and wherein the vial has a prismatic configuration and further has a rectangular cross-section complementary to that of the recess in the stick.

3. A lid lifter and a combined water sampling device for a swimming pool comprising an elongated stick having one end provided with a reduced cross-sectional area, a prong carried by the reduced cross-sectional area and extending transversely therefrom from at least one side of the reduced cross-sectional area, whereby the prong may be inserted beneath the removable lid of a swimming pool skimmer to lift the lid, a rectangular cross-sectioned sampling vial open at one end and closed at the other end, the stick having an intermediate portion with a complementary transverse recess formed therein to receive the vial, the closed end of the vial being disposed towards the one end of the stick, and the open end of the vial extending laterally beyond both adjacent respective surfaces of the stick, whereby the stick may be inserted into the pool and lifted out to obtain a water sample in the vial.

* * * * *